(12) United States Patent
Glowczwski et al.

(10) Patent No.: US 11,944,774 B2
(45) Date of Patent: *Apr. 2, 2024

(54) VASCULAR ACCESS CHANNEL AND METHODS

(71) Applicant: Voyager Biomedical, Inc., Houston, TX (US)

(72) Inventors: Alan Glowczwski, College Station, TX (US); Robert Smith, Missouri City, TX (US); Peter Smith, Houston, TX (US); Nathan Borgfeld, Austin, TX (US)

(73) Assignee: VOYAGER BIOMEDICAL, INC., Houston, TX (US)

( * ) Notice: Subject to any disclaimer, the term of this patent is extended or adjusted under 35 U.S.C. 154(b) by 523 days.

This patent is subject to a terminal disclaimer.

(21) Appl. No.: 17/164,058

(22) Filed: Feb. 1, 2021

(65) Prior Publication Data
US 2021/0228855 A1  Jul. 29, 2021

Related U.S. Application Data

(63) Continuation of application No. 15/525,320, filed as application No. PCT/US2016/031110 on May 6, 2016, now Pat. No. 10,905,867.

(Continued)

(51) Int. Cl.
*A61M 39/02* (2006.01)
*A61L 31/04* (2006.01)

(Continued)

(52) U.S. Cl.
CPC ........ *A61M 39/0208* (2013.01); *A61L 31/04* (2013.01); *A61L 31/046* (2013.01);

(Continued)

(58) Field of Classification Search
CPC .............. A61M 1/3661; A61M 1/3659; A61M 39/0208; A61M 39/06; A61M 39/02;

(Continued)

(56) References Cited

U.S. PATENT DOCUMENTS 5,562,617 A * 10/1996 Finch, Jr. ............... A61F 2/064
    623/1.1
2006/0247605 A1 * 11/2006 Edoga ................. A61M 1/3655
    606/151

(Continued)

*Primary Examiner* — Tiffany Legette
(74) *Attorney, Agent, or Firm* — Talem IP Law, LLP

(57) ABSTRACT

An embodiment includes a vascular port comprising: first and second portions that are not monolithic with each other; wherein: (a)(i) the first portion includes a first arcuate surface to contour to a first portion of a vessel and the second portion includes a second arcuate surface to contour to a second portion of the vessel; (a)(ii) the first and second portions couple to one another around the vessel when implanted to form a central chamber that houses the vessel; (a)(iii) the first portion includes a port that includes a funnel with a funnel surface that narrows as the funnel surface approaches the central chamber; (a)(iv) the central chamber includes a central longitudinal axis and the funnel includes a central vertical axis that is orthogonal to the longitudinal axis; (a)(v) the second portion includes a hardened, non-compliant surface that intersects the vertical axis.

14 Claims, 12 Drawing Sheets

Related U.S. Application Data

(60) Provisional application No. 62/157,589, filed on May 6, 2015.

(51) Int. Cl.
  *A61L 31/14* (2006.01)
  *A61M 1/14* (2006.01)
  *A61M 39/06* (2006.01)

(52) U.S. Cl.
  CPC .............. *A61L 31/146* (2013.01); *A61M 1/14* (2013.01); *A61M 39/02* (2013.01); *A61M 39/06* (2013.01); *A61M 2039/0205* (2013.01)

(58) Field of Classification Search
  CPC .......... A61M 39/0229; A61M 39/0235; A61M 1/3655; A61B 17/3423
  See application file for complete search history.

(56) References Cited

U.S. PATENT DOCUMENTS

| | | | |
|---|---|---|---|
| 2011/0213309 A1* | 9/2011 | Young | A61B 17/3423 604/93.01 |
| 2012/0046515 A1* | 2/2012 | Woo | A61M 60/585 600/16 |
| 2012/0245536 A1* | 9/2012 | Gerber | A61M 39/0208 604/288.01 |

* cited by examiner

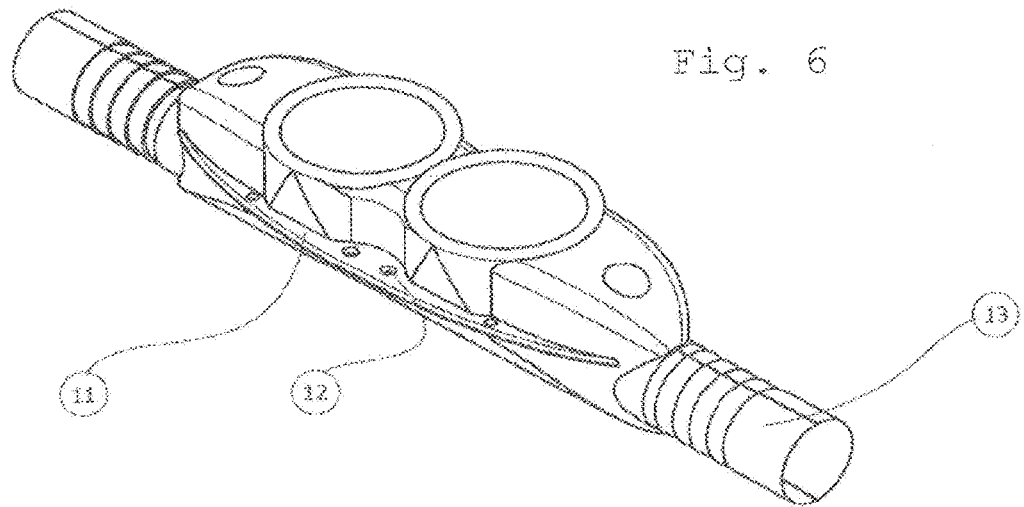
Fig. 6
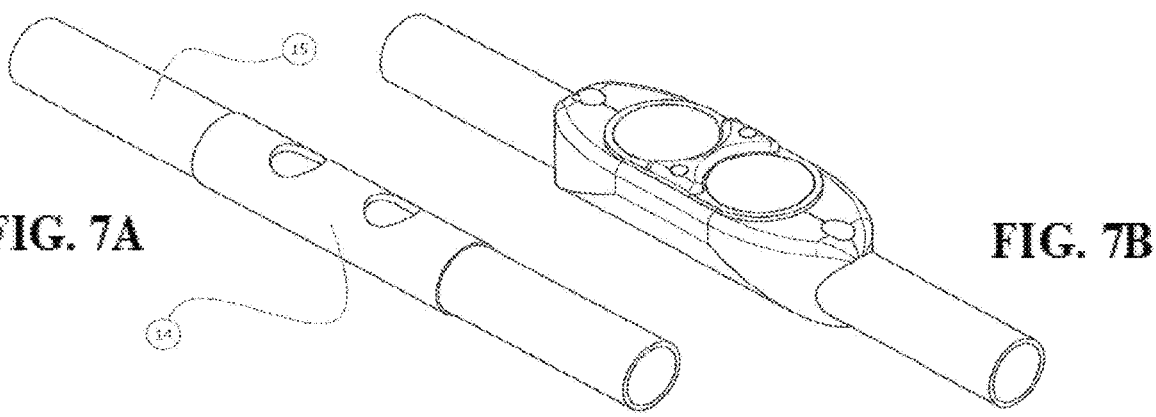
FIG. 7A
FIG. 7B
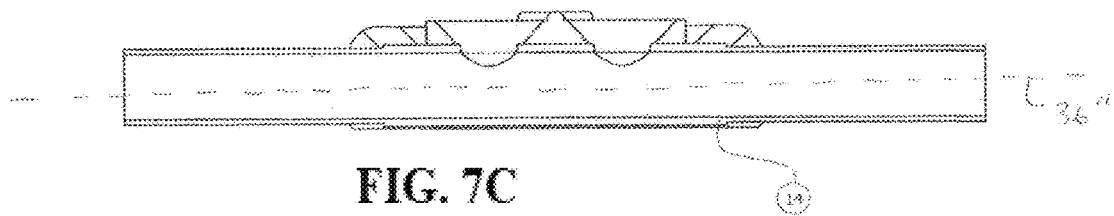
FIG. 7C

VASCULAR ACCESS CHANNEL AND METHODS

CROSS-REFERENCE TO RELATED APPLICATIONS

This application is a continuation application of U.S. application Ser. No. 15/525,320, filed May 9, 2017, which is a United States National Phase Entry of International Application No. PCT/US2016/031110, filed May 6, 2016, which claims priority to U.S. Provisional Patent Application No. 62/157,589 filed on May 6, 2015 and entitled "Ported Vascular Access Channel," the content of which is hereby incorporated by reference.

TECHNICAL FIELD

Embodiments of the invention are in the field of medical devices and, in particular, vascular access methods and devices.

BACKGROUND

The kidneys constantly filter blood, removing toxic substances, bodily fluids, and waste. Patients with decreased kidney function often require dialysis machines to serve as artificial kidneys to clean the blood. End stage renal disease (ESRD) can be caused by a variety of conditions including diabetes, hypertension, glomerulonephritis, polycystic kidneys, and urological disease. As of 2010, approximately $40 billion dollars are spent annually in the United States on ESRD treatment, with a significant portion going towards dialysis treatment. Of the 550,000 people with ESRD in the US, approximately 400,000 are on some form of dialysis.

There are several vascular access methods currently utilized for hemodialysis. The most immediate form of access is a temporary dual lumen catheter placed through a vein, such as the jugular or subclavian. The catheter tip is often positioned in the superior vena cava or the right atrium of the heart to allow for the high flow rates needed for hemodialysis (at least 200 mL/min). This method provides immediate access when needed. However, catheters frequently cause problems in the veins they are fed through. Infection and thrombosis leading to subsequent scarring and occlusion of the vessels can occur.

An arteriovenous (AV) anastomosis can provide an alternative, long term solution using grafts or fistulas. Both the graft and fistula methods are surgical techniques often employed in the arms. Native peripheral arteries and veins are generally too narrow to accommodate the large flow rates required for hemodialysis. These techniques provide a way to enlarge a vein to a more appropriate diameter. In the case of an AV graft, an artificial vessel (often made of polytetrafluoroethylene, or PTFE) is tunneled through the subcutaneous tissues between an artery and a vein. After healing, the graft will provide a site for repeatable dialysis access. Grafts are not a preferred technique by Medicare however because they have a shorter lifespan when compared to arteriovenous fistulas, mostly due to infection risk from foreign material, the high-frequency of clot formation within the graft, or possibly the weakening of the graft due to multiple punctures.

AV fistulas are the current preferred method for hemodialysis access. Since they are created from the body's own tissue, there is less risk of infection. In addition, the fistulas have an increased long term patency rate. Despite these advantages, AV fistulas still have many drawbacks, including a prolonged period of maturation prior to use, poor maturation of the draining vein (it may not dilate to an adequate diameter to enable access), diminished circulation distal to the site (arterial steal), and difficulty cannulating the vein for dialysis. Fistula walls can weaken over time, becoming sites of aneurysms that can be a focus for thrombosis and infection, and therefore failure. The indications of a usable dialysis fistula are 1) sufficient diameter of the vein, 2) sufficient flow through the vein, and 3) an adequately superficial location under the patient's skin. If these conditions are not met, the anastomosis is considered immature. Early-stage fistula failure is defined as a fistula that never fully develops or fails within 3 months of its creation. A common cause of early-stage fistula failure is a stenosis in the vein, often located at the anastomosis. Causes of late-stage fistula failure (after 3 months) are difficulty cannulating the fistula, low flow rates, and thrombosis. It is clear that new methods are required which can eliminate or reduce the problems associated with current techniques.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 6: An embodiment depicting rudders, suture points, and flanges.

FIGS. 7A-7C: A concentric stent within a graft wall locking the graft in place within a port in an embodiment.

DETAILED DESCRIPTION

Figure 1:
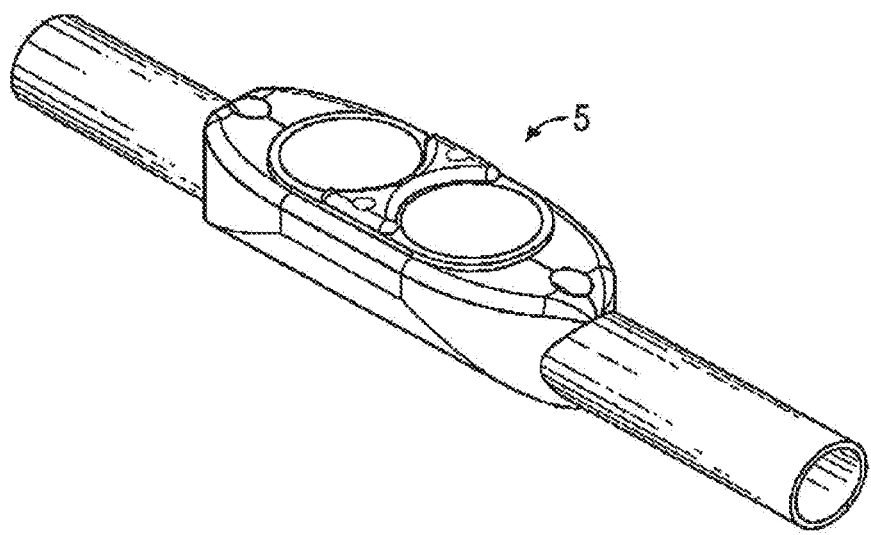
FIG. 1: A ported vascular access channel with biodegradable matrix scaffold in an embodiment.

In the following description, numerous specific details are set forth but embodiments of the invention may be practiced without these specific details. Well-known structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner.

There is a growing need to replace current hemodialysis access techniques with methods that allow for earlier use of long term vascular access and that minimize the chances of complications and failure of the access. Current methods can take time to "mature" and become usable, and can become blocked or unusable over time. However, embodiments described herein provide, for example, a long term access device that (a) provides a viable means for dialysis, (b) is simple to locate and access by the dialysis technician, (c) provides improved accessibility throughout the lifespan of the device, and (d) is usable shortly after surgery.

Embodiments described herein offer improvements including, but not limited to, the following. First, in an embodiment a port is assembled from multiple pieces: a bottom face, a top face featuring a central opening (termed the "needle well"), and a bioactive matrix scaffold situated within the needle well. These pieces shall join to produce a port capable of encasing a vessel to provide blood access. Second, in an embodiment the port is assembled without the use of a bioactive matrix scaffold and comprises the top and bottom faces. Third, in an embodiment a bioactive matrix scaffolding is included within needle well(s). This provides an immediate means of sealing the port after it is punctured, allowing for a faster turnaround time between implantation and use. The bioactive matrix scaffold may be punctured and will provide a substrate to initiate hemostasis, and over time will encourage infiltration of the body's own vascularized, fibrous tissues. A barrier of natural tissue will resist infection better than a typical silicone or urethane plug and encourage hemostasis after puncture. The bioactive matrix scaffold may either be permanent or degradable. Fourth, in an embodiment the port is easier to locate under the patient's skin than other subcutaneous grafts or fistulae which are more compliant and whose locations may be difficult to approximate by palpation. It also serves to guide the needle into the proper location within the lumen, eliminating some of the human error involved in obtaining proper vascular access. The port also prevents a needle from puncturing through the back wall of the vessel (e.g., graft), which is a common cause for blood loss into the subcutaneous tissue and subsequent hematoma formation (a complication that can result in lost access and the need for expensive intervention). Fifth, an embodiment adapts the port concept to a catheter, such that a subcutaneous catheter has the following advantages: (a) the bioactive matrix scaffold barrier encourages vascular tissue ingrowth (which allows infiltration into the device by lymphocytes to reduce infection), (b) the catheter would not be exposed to pathogens on the skin's surface, lowering infection risk, and (c) the catheter would retain the immediate usability of other vascular access catheters that are currently used for functions including hemodialysis, chemotherapy, and the like. Sixth, an embodiment includes angled side-entry points that allow simplified removal of thrombi from the graft by an interventional physician via a catheter or guide wire.

An embodiment creates a new form of vascular access to improve or replace existing methods. The embodiment facilitates access to a blood vessel or graft via a port apparatus which allows consistent endovascular access into the lumen of the vessel via needles inserted directly into the port. The port apparatus provides structural support, decreasing the amount of trauma incurred to the vessel wall or graft and diminishing the subsequent scarring and stenosis. In an embodiment, a bioactive matrix scaffold made of some combination of natural tissue and/or synthetic polymer prevents bleeding from the vessel and greatly decreases the maturation time of the fistula or graft. The port is located directly under the skin, enabling easy access to the vessel and limiting the risk of infection by utilizing the skin as a natural barrier to pathogens. This also addresses the current challenge of locating a viable access point; for instance, many dialysis patients are obese, and their AV fistulas may be hard to find and puncture successfully. Alternatively, due to collateral veins some fistulas never contain enough blood to dilate perceptibly. Because vascular access must often be performed multiple times per week, there is little time for skin to heal between treatments. The needle wells guide the needle down into the vessel while providing a greater surface area for needle puncture. This enables vascular access technicians to puncture in different locations along the skin's surface, thus preventing skin breakdown and giving each site a chance to heal. In addition, technicians are able to advance the needles at different angles because the port directs the needle's path directly into the vessel lumen. The rigid back wall of the port functions as a stopping point for the needle, thereby preventing through-and-through punctures. Access is therefore simplified, enabling even an inexperienced person to access the vessel, which may result in an increased use of home-based vascular access treatments and a new level of independence for patients, including dialysis patients who must often visit a dialysis clinic three times per week. Angled side-entry points adjacent to the needle wells will function as entry sites for wires/catheters that interventional physicians use to clean thrombi out of clotted grafts thus simplifying this procedure. Though embodiments have great utility for dialysis patients, such embodiments have capabilities as a long-term and reliable blood-access method and are therefore suitable for use in plasmapheresis or as a chemotherapy or drug-delivery system for patients with chronic illnesses that require frequent infusions of nutrients, antibiotics, clotting factors, parenteral nutrition, or other injectable therapies.

As used herein the term "ported vascular access channel" is meant to refer to the compartment through which blood or other fluid (e.g., biological fluid) may flow in addition to the accompanying features as described herein. That fluid compartment may include a natural vessel, a synthetic graft, catheter with subcutaneous port, and the like.

An embodiment comprises a port 5 surrounding a blood vessel or graft or catheter or other blood access channel to be used for permanent blood access (FIG. 1). The port may be fabricated from a biocompatible plastic, metal, or ceramic. Such materials include, for example, titanium, Poly Ether Ether Ketone (PEEK), aluminum oxide, and the like.

Figure 2:
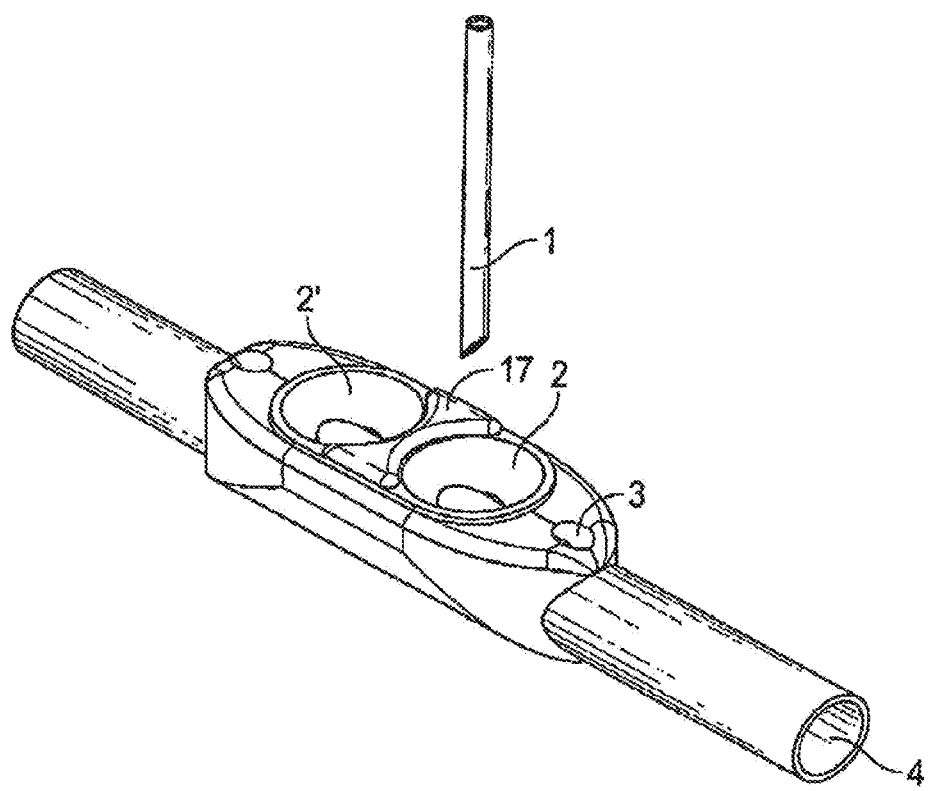
FIG. 2: A ported vascular access channel with biodegradable matrix scaffold removed in an embodiment.

In an embodiment the needle puncture site(s) is palpable from the surface of the patient's skin and is composed of one or more wells 2 (FIG. 2). The needle wells are cavities leading from the port's outer surface to the inner lumen of the vessel 4 and are contoured such that the needle 1 is guided directly into the inner lumen. They may be funnel-shaped in order to increase the total skin surface area that may be punctured by the needle to allow the skin a chance to heal. A preferred embodiment of the wells may resemble a trough 18 (FIG. 3) that includes room for many puncture sites down the length of the port. The advantage of this guided-needle entry system is the ease of access into the vessel. Fewer attempts will be necessary to achieve a successful puncture, improving patient comfort, lowering risk of infection, and sparing the vessel from increased trauma and scarring. Additionally, a simplified vascular access method may enable home dialysis.

In an embodiment the bottom face of the port 9 is rigid to prevent rupture of the vessel's back wall 10 by the needle. This is necessary for preventing loss of blood into the extraluminal space where it may cause a hematoma and block access into the vessel. In an embodiment the bottom face of the port may have a layer of softer material in which to embed the needle and assist in immobilizing it. This softer material may consist of, but is not limited to, a low-density silicone sheet or other soft plastic. The very back layer of the port may be formed from a high-hardness material such as an alumina ceramic or metal that resists damage by the needle, which is made of a stainless steel in an embodiment.

An embodiment of the port (FIG. 4) comprises multiple pieces that are assembled in differing fashions. An embodiment may include a sleeve 6 and needle well insert 7 which may be assembled from separate materials in order to maximize useful properties of each material. The needle well insert may be formed from a high-hardness material such as a titanium alloy or alumina ceramic in order to minimize wear debris created by friction between the well and the needle. In addition, both of these materials are very corrosion-resistant and have an excellent track record in the field of orthopedic implants.

In an embodiment the needle well(s) enable a method of preventing blood from leaking out of the port immediately following vascular access and when the device is not in use. An embodiment involves filling the well with a bioactive matrix scaffold 8 (FIGS. 4 and 5) that serves as an initial impediment to blood loss by stimulating hemostasis and, over time, encouraging vascular tissue ingrowth. This will transform the bioactive matrix scaffold into a self-healing barrier. This tissue has the ability to aid in clot formation to stop bleeding following vascular access and is not as susceptible to developing the type of latent biofilm infection that is often associated with implanted materials. Bacteria introduced into the port can be eradicated by the body's own immune system, improving the device's long-term integrity and usefulness. In addition to or instead of the biodegradable matrix scaffold, the needle well(s) may contain a bactericidal component such as silver nitrate that could aid in preventing the development of a biofilm within the well. The presence of the bioactive matrix scaffold within the well should also decrease the waiting period before the device can be used to access blood. Current arteriovenous grafts require several weeks before they can be accessed, and fistulas may require months. A ported vascular access channel with a hemostatic bioactive matrix scaffold is a solution that is usable much sooner following implantation, an important option for acute renal failure patients.

Though the needle wells are intended to maximize the surface area that can be punctured by a needle, the presence of a barrier of bioactive material/natural tissue within the port's needle wells make it well-suited for the "buttonhole technique." In the buttonhole technique, the needle is inserted by the technician at the exact same point for each treatment. In fistulas this method has shown to be effective in decreasing patient discomfort, decreasing bruising, lowering infection rates, and enabling home dialysis. With a barrier of natural, self-healing tissue within the port, the use of the buttonhole technique could afford these same advantages to ported grafts or catheters.

A number of materials and additives exist which may serve as constituents of the bioactive matrix scaffold 8, which may comprise any number of biocompatible natural or synthetic materials, including without limitation, polymer foams, poly ethylene glycol (PEG) hydrogels, polyglycolic acid (PGA), polylactic acid (PLA), poly(lactic-co-glycolic acid) (PLGA), glutaraldehyde adhesives, fibrin sealants, cyanoacrylates, collagenous compounds, electrospun fabrics, decellularized extracellular matrix, or any other biocompatible material, degradable or not, that will encourage the formation of vascularized tissues. The bioactive matrix scaffold may either be inserted at the time of manufacture, or alternatively at the time of implantation, whichever is most expedient depending on the desired material. The interfaces between the various parts of the device may be filled with cyanoacrylates or other space-filling gels/foams (e.g., a polyurethane shape memory polymer foam)/adhesives to prevent potential spaces from harboring bacteria, or in addition/alternatively the interfaces may be composed of bactericidal materials such as silver-doped ceramic.

In an embodiment a material for use as the bioactive matrix scaffold is polyurethane urea foam, which has demonstrated excellent vascular ingrowth in experiment. This material may be formed separately and later adhered to the port, or instead may be cured within the port. An embodiment includes a port material with large-diameter open pores (e.g., open cell polyurethane foam). As a result, the polyurethane urea polymer can infiltrate and anchor itself within the cells during curing. In this method, vascular tissue can infiltrate the entire implant, with the port material serving as a rigid "skeleton" that guides the needle safely into the lumen of the vessel.

An embodiment includes a method of sealing the ported vascular access channel. The method utilizes a bioactive matrix scaffold that is gradually replaced with biological tissue. However, other embodiments use methods of sealing the channel and may also include some sort of permanent plastic rubber membrane or mechanical valve. An embodiment includes no method of sealing the port, instead allowing the subcutaneous tissues to fill the needle wells naturally. This process may be aided by specific port materials, certain port structures, and optimized port surface coating. An embodiment without the bioactive matrix scaffold comprises a titanium alloy port composed of a meshwork of large, open pores that allow excellent tissue infiltration and adhesion. In an embodiment pores are formed from nanotubes that foster tissue ingrowth and may further hinder bacterial growth. This enables not only the needle well, but the entire device, to be infiltrated by natural tissues, improving anchoring and eliminating spaces that may harbor bacteria. Such a structure is producible by powder metallurgy. Titanium and its alloys are naturally extremely biocompatible as they naturally produce an oxidized layer of $TiO_2$ on their surface which is very stable at physiologic pH. In addition, processes have been described to further improve Titanium's biocompatibility, including an anodization process which forms surface $TiO_2$ nanotubes that improve tissue adhesion, and the "sol-gel" technique which produces layers of ceramic over the titanium, including the $SiO_2$-based "bioglass" 45s5 which is known to encourage excellent tissue growth.

Figure 4:
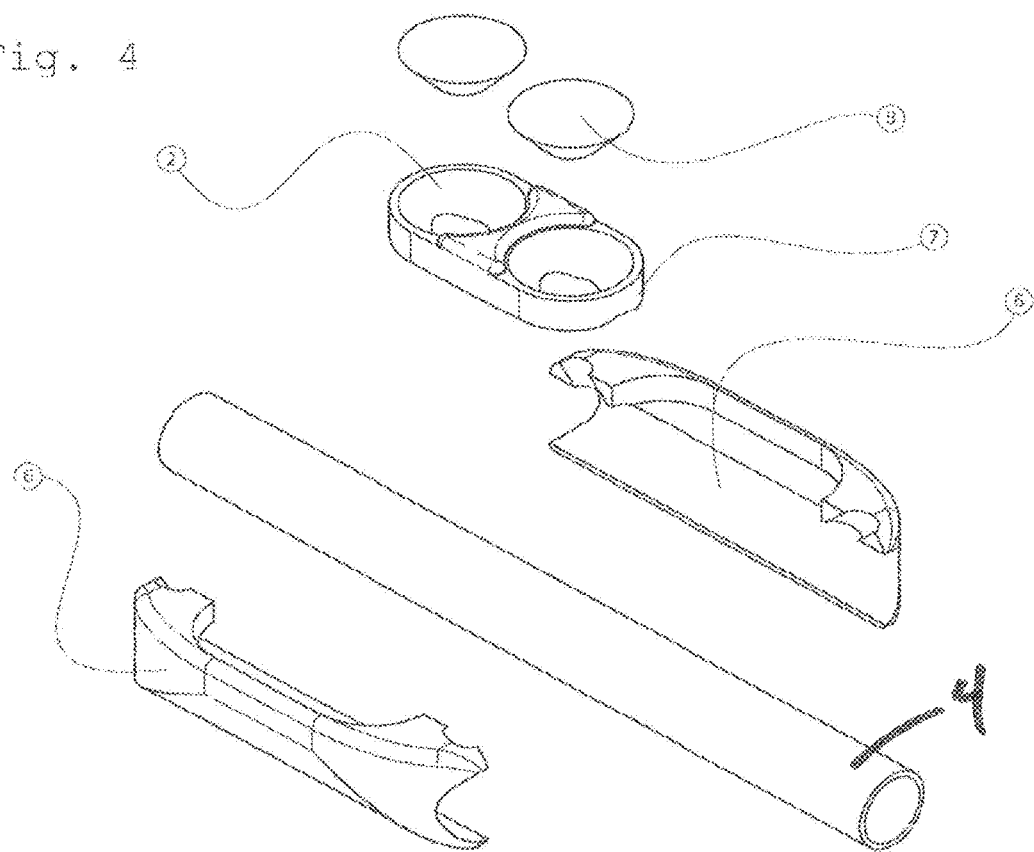
FIG. 4: An exploded view of a ported vascular access channel in an embodiment.

Attempts to puncture current arteriovenous fistulas are complicated by the pliability of these vessels, as they often collapse rather than allow a needle to pierce them successfully. However, in an embodiment the port provides radial support to the vessel wall and holds it open during the needle's entry. This may be accomplished through surface finishes or coatings within the channel of the port that encourage soft tissue attachment between the port and the vessel wall. An embodiment includes a bioactive matrix scaffold which extends from the needle well into the port channel and surrounds the vessel to stimulate this attachment (FIG. 4, area 6). An embodiment includes the use of an adhesive applied within the port channel, such as a cyanoacrylate glue, which results in adherence of the vessel wall to the surface of the port channel. Alternately, in an embodiment in which the port surrounds an artificial vessel such as a PTFE graft, patency can be assured via a concentric support 14 embedded into the graft wall 15 (FIGS. 7A-7C). Application of a radial force to the vessel wall also prevents "pseudoaneurysms," which form when blood leaks into the interstitium adjacent to a damaged vessel and can end up sealing off the vessel and preventing access. This feature reduces damage to the vessel, prevents leaking, and disallows the "mass effect" of a growing hematoma to occlude the vessel. Such a configuration forces the vessel to maintain patency by disallowing the formation of aneurysms, pseudoaneurysms, or occlusions caused by external pressure.

Figure 12:
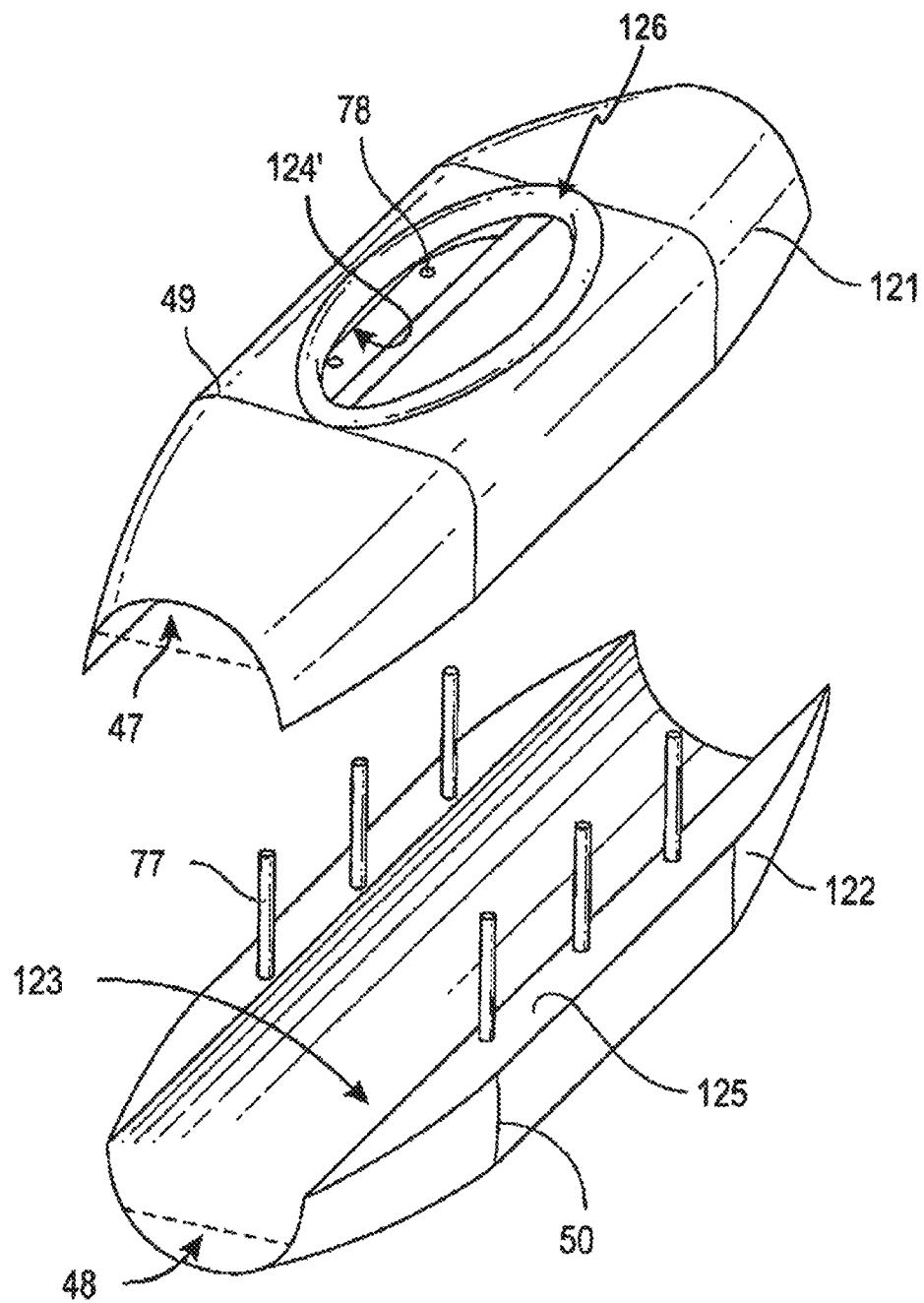
FIG. 12: A tunneled contour with prongs in an embodiment.

As seen in FIG. 12, an embodiment includes a method of constructing the device as follows. A port, which comprises a bottom face 122 and a top face 121, where the top face contains a needle well, may be manufactured out of titanium or titanium alloys such as Ti6Al4V via powder metallurgy or other process to bestow the port with a meshwork of pores or channels of any size. These pores may be varied in size on the outer surfaces of the device to encourage prolific tissue ingrowth, and with additional pores on the surface of the trough or funnel (2) and bottom face 123 (e.g., pores that are small enough to prevent passage of a needle). The top and bottom faces will encircle an arteriovenous fistula, though they may or may not make direct contact with one another and instead leave a small gap between them. For example, portions 121 and 122 may not fit flush against each other when assembled during implant.

In an embodiment, within the meshwork structure on the top and bottom faces are opposing suture holes 12 into which a resorbable suture may be placed by the surgeon in order to approximate the two faces. By using resorbable sutures and allowing for a gap (not shown in FIG. 6 and present in some embodiments of FIG. 6 but not others) to exist, the possibility that a biofilm might form between the two faces is diminished, and the vessel retains its natural compliance, which is necessary should the vessel dilate or require balloon angioplasty, or if proliferating tissue begins to narrow the vessel's lumen. Into this port may be formed the bioactive matrix scaffold consisting of the polyurethane urea foam as described above.

Figure 14:
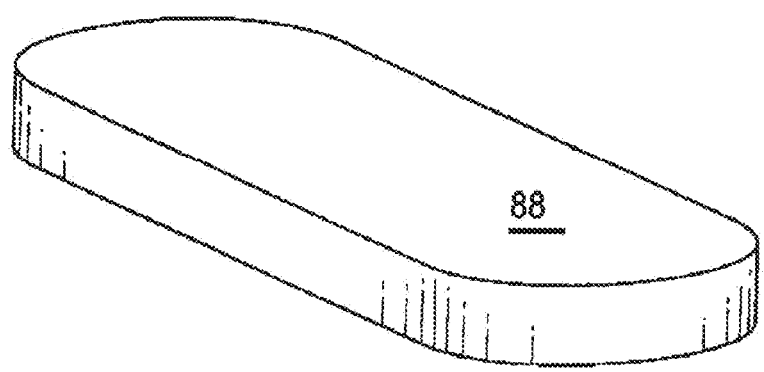
FIG. 14: A sheet of bioactive matrix scaffolding in an embodiment.
Figure 13:
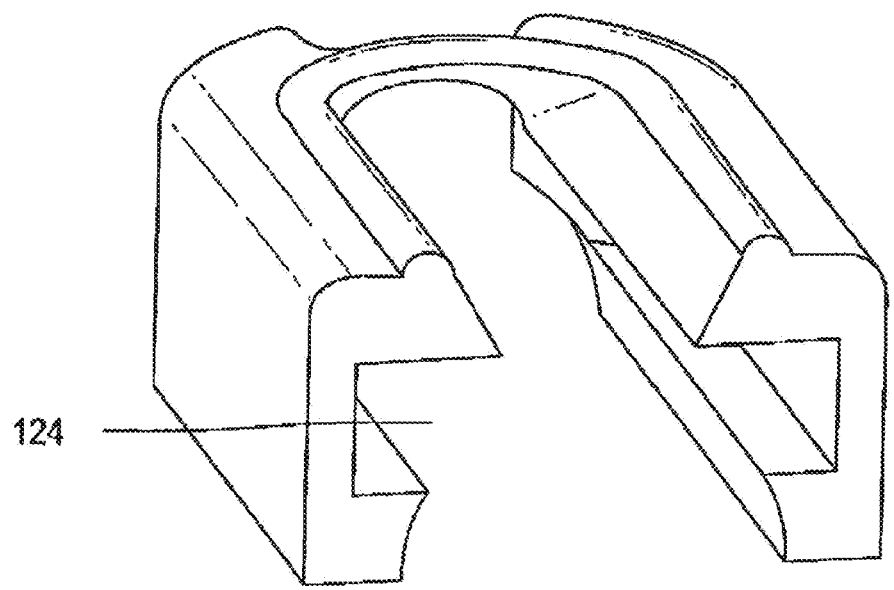
FIG. 13: A cross-section of top face portion showing recess for bioactive matrix scaffold in an embodiment.
Figure 15:
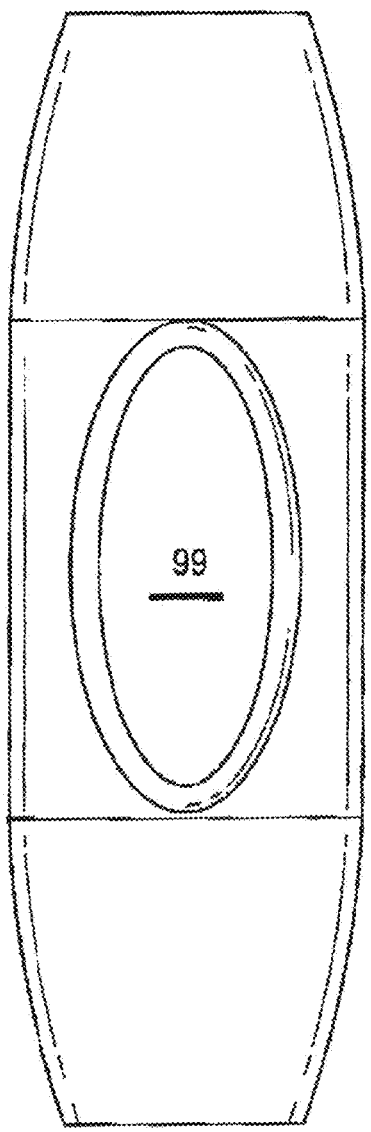
FIG. 15: A fish-mouth shape of a trough in an embodiment.

In an embodiment the device utilizes top and bottom faces 121, 122 (FIG. 12) which are approximated by prongs 77 on the bottom face (and/or top face). The prongs fit into corresponding holes on the opposing face but do not fasten the faces flush together. This allows for expansion of the center channel and retains the vessel or fistula's natural compliance while preventing shear stress at the interface between the top and bottom faces. In an embodiment the device narrows on its ends to allow for "tunneling" through tissue, and it may feature a roughened or porous surface which is optimized for tissue adhesion. For example, a tissue ingrowth promoting surface may have a texture provided by compaction and sintering of metallic beads (e.g., titanium beads) or powders onto the port. In other embodiments the surface may be formed by machining, sandblasting, laser etching, and/or injection molding. Within the top face is a recess 124 (FIGS. 12, 13) into which a sheet of the bioactive matrix scaffolding material 88 (FIG. 14) is inserted. The scaffold material may be subject to deformation as it is populated with contractile connective tissue; to maintain its desired geometry the scaffold may be anchored by a ductile retention ring that can be fed through the scaffold, or by extending the length of the prongs 77 on the bottom face 122 such that they pierce the scaffold once the device is assembled around the vessel. The trough on the top face of the device may have an irregular "fish-mouth" shape 99 (FIG. 15), being narrower on its ends and wider at its center, to allow two dialysis needles to cross side-by-side while engaged within the trough.

An embodiment includes a method of constructing the invention for use with a synthetic vascular graft. A vascular graft, which may be made of expanded polytetrafluoroethylene (ePTFE) material, is surrounded by a concentric support or stent 14 of nitinol or other rigid material which is then encapsulated by an additional layer of ePTFE 15 (FIGS. 7A-7C). The stent provides the graft with radial strength during needle puncture as well as a larger profile with which to lock into place within the port 5 (FIG. 4). In an embodiment, the port, made of Poly Ether Ether Ketone (PEEK) or one of any number of biocompatible materials, comprises a sleeve with a rigid back wall that fits around the graft, concentric with the rigid stent, locking the stent in place within the sleeve 6. A needle well insert 7 comprising a high-hardness material such as a ceramic or titanium will lock into the top face of the sleeve 6 to provide a surface that will identify the location of the graft beneath the skin, guide the needles into the lumen 4 of the graft, and resist wear debris from shear stresses applied by the needle. The top surface of the needle well insert may be contoured 17 so as to help identify the appropriate location to insert the needles (FIG. 2). Within the wells themselves is biodegradable matrix scaffold 8, which may comprise a polyurethane urea foam or any number of well-known biocompatible natural or synthetic materials as previously described.

An embodiment includes a method of adhering the port to the graft material as follows. The graft is fed through a channel down the long axis of the port and fastened to the port with a cyanoacrylate and/or fibrin adhesive. The needle well insert is included, and the biodegradable matrix scaffold as described above may be placed within the needle well insert at this time or injected into the wells during the implantation surgery. As before, the interfaces between the various materials may be filled with cyanoacrylates or epoxies to prevent potential spaces from harboring bacteria, and/or the interfaces may be composed of bactericidal materials such as silver-doped ceramic.

An embodiment includes an alternative method of adhering the port to the graft material as follows. The port itself is assembled into one solid piece, including the needle well insert. At the proximal and distal ends of the port are flanges 13 (FIG. 6) onto which the graft tubing may slide concentrically, eliminating the need to adhere the graft material to the inside of the port. In this embodiment the inner channel of the port may receive various treatments to improve hemocompatibility, such as heparin or DLC coatings, which have been shown to reduce clotting.

An embodiment includes a method as follows. After using standard surgical technique for the creation of an AV fistula, the port, comprising a top and bottom face, is placed circumferentially around the fistula and the two faces are approximated using resorbable sutures. The port is oriented such that the top face is parallel with the surface of the patient's skin. The fistula may be mobilized in order to place the port at an appropriate depth such that it can be seen/palpated beneath the skin. The resorbable sutures may also be used to anchor the port in this position while the patient's own tissue begins to make its attachments to the port.

In an embodiment, a similar method can be employed to install the implant around an existing vessel. A port which separates into two sections, a back plate and a front plate or two symmetrical side plates, is fastened around an existing graft, arteriovenous fistula, or other vessel from which it is desirable to access blood. This may be done to enclose an aneurysm and prevent it from bursting or to simplify the localization of hard-to-find vessels.

An embodiment includes a method as follows. Using standard surgical technique for the creation of an arteriovenous anastomosis with synthetic graft material, the graft and attached port are mobilized under the patient's skin such that the top of the needle well insert faces outwards to allow for needle access. Unlike typical arteriovenous grafts, which are usually quite long so as to distribute damage from needles, the port will be the sole entry point into the lumen, and excessive graft length will therefore be unneeded. This means the amount of implanted foreign material can be reduced, and with it the risk of clotting and infection. Though kinks were a cause for concern in prior grafts, the majority of the material in these grafts will not be punctured, and therefore a thicker/stiffer material can be used to provide additional stiffness and reduce the risk of kinks, especially at the junctions between the compliant graft and the rigid port.

Vessel length and resistance are proportional; for instance, a $\frac{1}{3}$ reduction in graft length generally results in a $\frac{1}{3}$ reduction in graft resistance and therefore an increase in blood flow, which may or may not be desired. To combat this reduction in resistance, the graft diameter can be decreased, as resistance is proportional to the inverse of the radius to the fourth power. A typical graft diameter is 6 mm, so to cancel out a theoretical $\frac{1}{3}$ reduction in resistance due to a shortened length of the graft, the diameter of the graft can be decreased to 5.4 mm. The end result will be an equivalent resistance to flow considering: (a) Resistance $\propto$ Length, and (b) Resistance $\propto (1/\text{Radius}^4)$.

An embodiment of the ported vascular access channel may include needle wells which are not on the top face of the device but rather on the sides. This configuration decreases the height of the implant in favor of a greater width and may be preferable in cachectic patients or those with little excess tissue in which to imbed the device.

Figure 9:
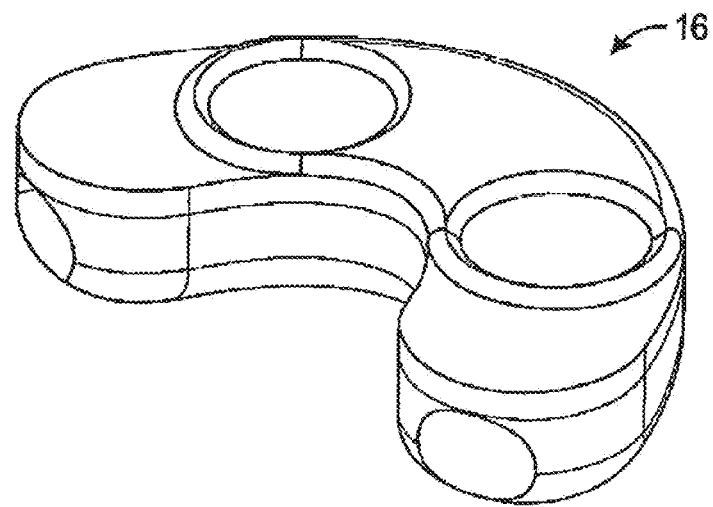
FIG. 9: A "u"-shaped port configuration in an embodiment.

An embodiment of the ported vascular access channel may contain a lumen which is not cylindrical in shape, but may instead be contoured as an "S" or "U" 16 (FIG. 9) or other configuration to optimize its interface with the patient's anatomy and the location of his or her vasculature. These alternative configurations may also serve to help vascular surgeons tunnel the device under the skin to its optimal location without causing kinks to form in the vessel.

Embodiment methods of coupling the top and bottom faces of the port to each other include, but are not limited to, biocompatible plastic adhesives, interlocking teeth or snaps, ties, sutures, pegs, screws, or other fasteners. An embodiment comprises suture holes in the top and bottom port faces through which bioresorbable sutures may be stitched. This would approximate the top and bottom faces during the implantation surgery and the period immediately following while the patient's natural tissues started to adhere to and anchor the separate parts. As this takes place, the resorbable sutures degrade and the top and bottom faces are no longer firmly fastened together. This allows the vessel within the port to retain its compliance, especially should the vessel later need another procedure such as balloon angioplasty. It also prevents the formation of an impenetrable junction between the top and bottom faces, which otherwise could be colonized by bacteria.

As described previously, an embodiment of the invention includes top and bottom faces which are not in direct association, instead leaving a gap present between them. The end result of this configuration is improved vessel compliance and a reduced risk of biofilm formation at the juncture between the two faces of the port. For example, with FIG. 12 portions 121 and 122 may not fully meet along surface 125 because, for example, pegs 77 may be longer than their reciprocal female portions in piece 121.

Figure 10:
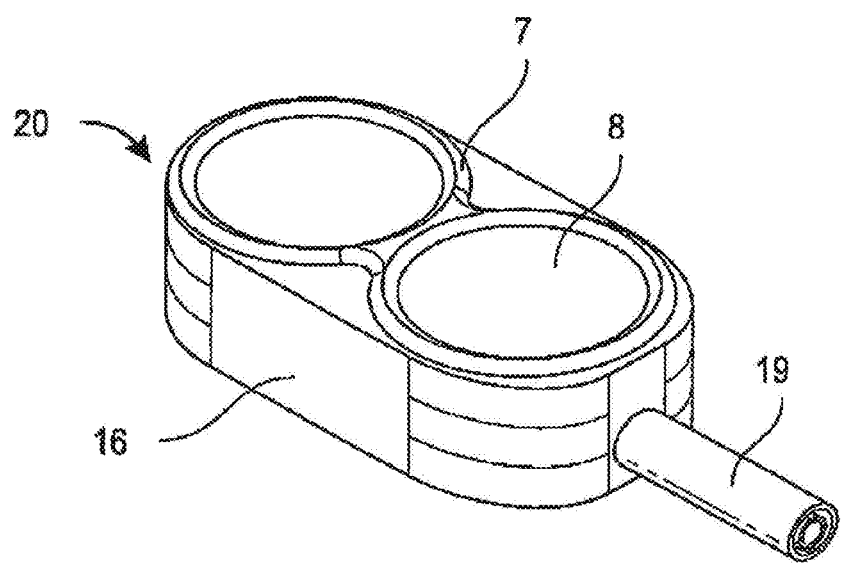
FIG. 10: A ported vascular access channel with catheter in an embodiment.

An embodiment of the device is a ported catheter (FIG. 10), which could be assembled as follows. A standard central line catheter 19 may feature a port system 20 comprising the port body as a single piece 16 rather than as a top and bottom face, needle well(s) 7, and bioactive matrix scaffold 8 as previously described.

Since it is often the case that dual-lumen central line catheters, with one lumen for withdrawing blood and one lumen for replacing it, become "blocked" by the suction they create as they withdraw blood, an embodiment alters the geometry of the catheter tubing to include three lumens. Two "withdrawal" lumens, in opposition to one another, pose little or less risk of becoming blocked even if one lumen is suctioned to the wall of its vein. An embodiment may include a port with internal geometry to accommodate such a catheter 19. In an embodiment, the distal tip of the central lumen may extend past the edge of the outer lumens so that blood which is replaced through the central lumen re-enters the patient's circulation downstream of the outer lumens, thereby minimizing the amount of blood recirculated through the dialysis machine. Also, since subcutaneous implants incur a significant amount of tissue ingrowth which may complicate their removal, the catheter may also be equipped with a "handle" which serves as a grasping point during explantation of the catheter.

Figure 11:
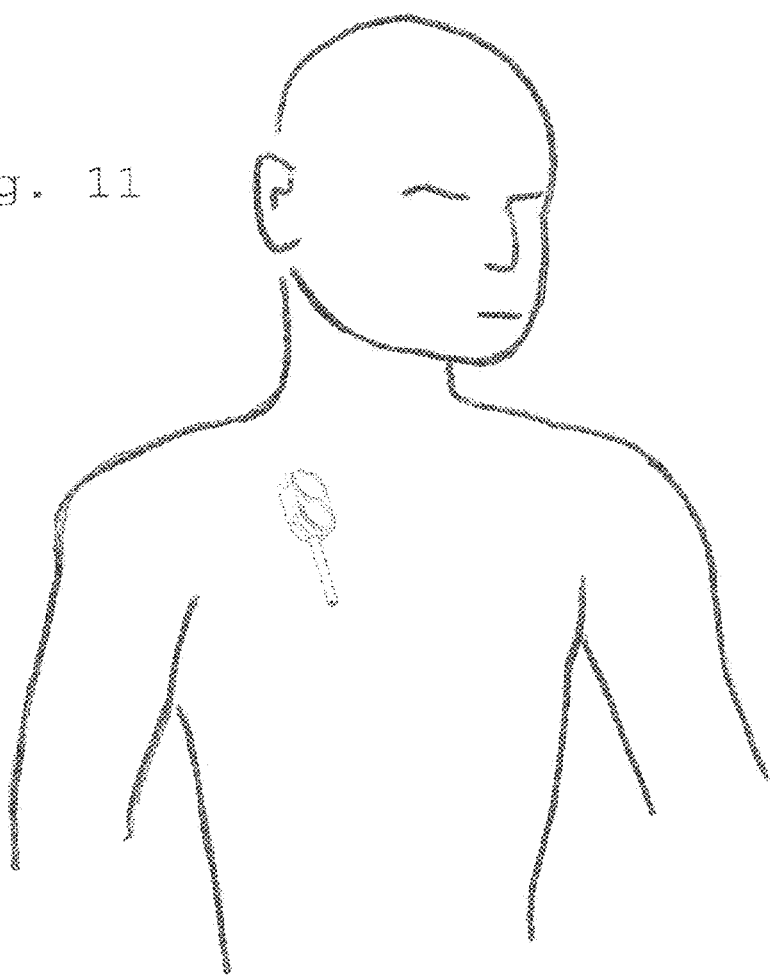
FIG. 11: A ported vascular access channel with catheter implanted in patient's thorax in an embodiment.

An embodiment includes a method as follows. Following standard procedure for inserting a central venous line into the patient's internal jugular, axillary/subclavian, or femoral veins, the head of the catheter, which comprises the port system as described previously, is tunneled beneath the skin of the patient to remain in the subcutaneous tissue (FIG. 11) where it can be accessed periodically for fluid removal/injection.

In an embodiment an anchoring system (FIG. 6) may include a series of rudders or keels 11 and suturing sites 12 which may be included in the body of the port or other synthetic material, including a graft if one is used, to stabilize and properly orient the port for puncture. Corrugated edges, a roughened outer surface, and the inclusion of collagen deposits or other tissue-promoting substances may encourage in-growth of tissue around the device and its anchors, further stabilizing it. It is well-known that porous materials demonstrate improved tissue ingrowth and anchoring, and many surface-treatments have been described which also encourage this behavior.

Along the surface of the apparatus there may be angled "side-entry points" 3 (FIG. 5) that extend from the surface of the device to the lumen of the vessel. These side-entry points will allow a shallow entry into the lumen of the graft and direct small guide wires or catheters which can be used to remove thrombi that form within the graft, a frequent and costly failure mode of vascular access grafts. This expedites the physician's access into the graft, making for a quicker, simpler, and potentially less-costly procedure.

An embodiment of the ported vascular access channel may include radiopaque markers fixed to the device to orient physicians and surgeons who are implanting/revising/accessing the device for whatever reason. This is to enable healthcare providers to utilize radiographic imaging to identify appropriate sites for withdrawal/injection of fluid or to correctly locate the side-entry points, the channels through which interventional physicians may insert guide wires or catheters to remove thrombi, as discussed previously.

An embodiment provides advantages that translate into a permanent vascular access system that will be usable shortly after implantation, retains its patency, is simple to use and maintain, requires less intervention/revision, and is less prone to infection than other previous access methods. These features will have a positive impact on patients who require hemodialysis, plasmapheresis, chemotherapy, parenteral nutrition, or any other condition requiring frequent blood access.

While not specifically shown, and embodiment provides bioactive scaffolding surrounding the vessel (e.g., between vessel 4 and the sidewalls of shell components 6 of FIG. 4).

Figure 3:
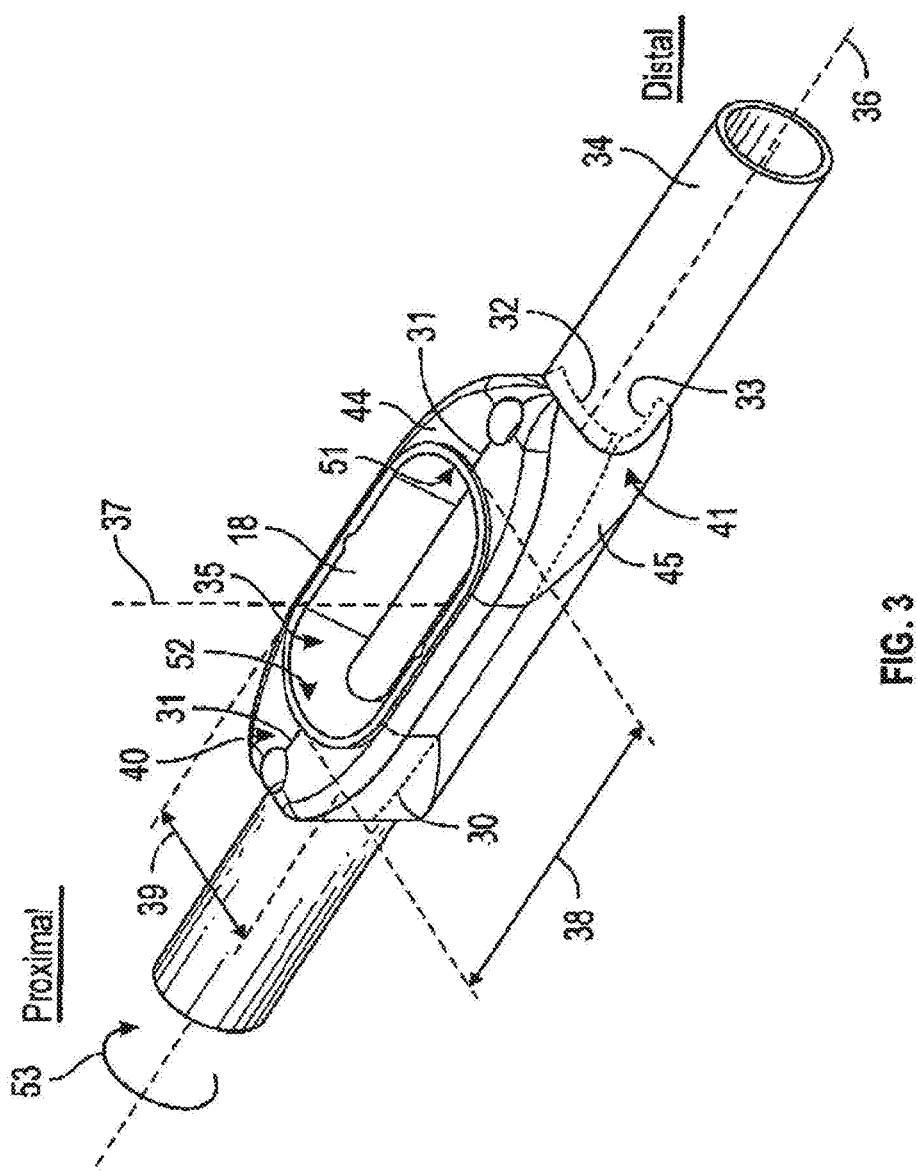
FIG. 3: An embodiment in which needle wells resemble a "trough".

An embodiment includes a vascular port comprising: first and second portions 44, 45 that are not monolithic with each other (FIG. 3). For example, portions 44, 45 may couple together along junction 31 in a "side-by-side" arrangement or along junction 30 in an "over-under" arrangement. The first portion includes a first arcuate surface 32 (assuming an over-under arrangement) to contour to a first portion of a vessel 34 and the second portion includes a second arcuate surface 33 to contour to a second portion of the vessel. In other embodiments such contouring is not present.

The first and second portions couple to one another around the vessel when implanted to form a central chamber that houses the vessel. A central chamber is defined by element 46 in FIG. 5. In this picture vessel 4 is flush to the upper and lower walls of chamber 46 but this may not be the case in all embodiments. In some embodiments there may be space between the chamber walls and the vessel or there may be tissue scaffolding (e.g., a shape memory polymer foam or hydrogel) that snugly couples the vessel to the walls of the chamber.

Figure 5:
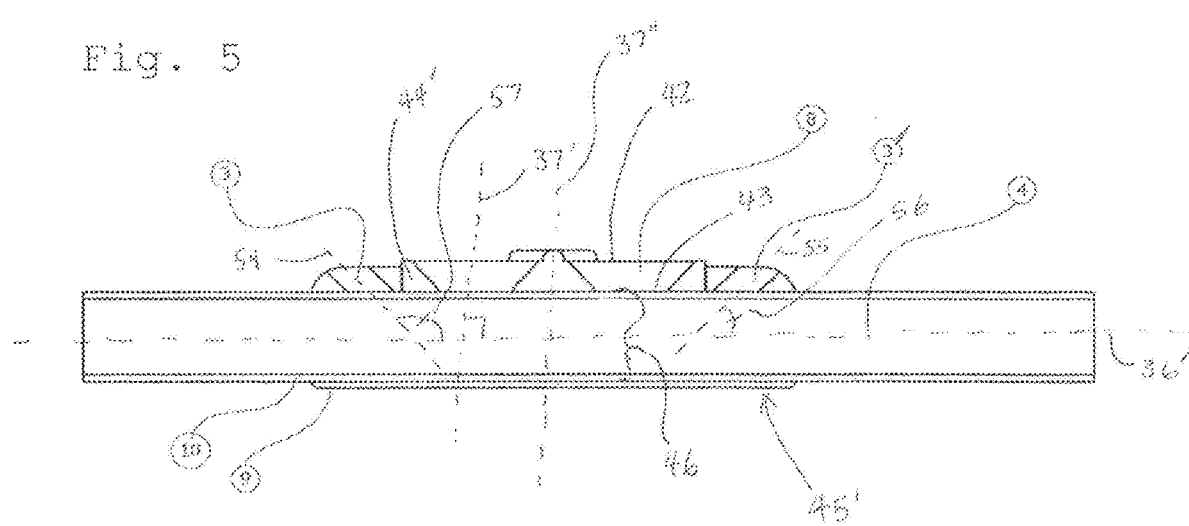
FIG. 5: A cross-section view depicting a biodegradable matrix scaffold and rigid back wall in an embodiment.
Figure 8:
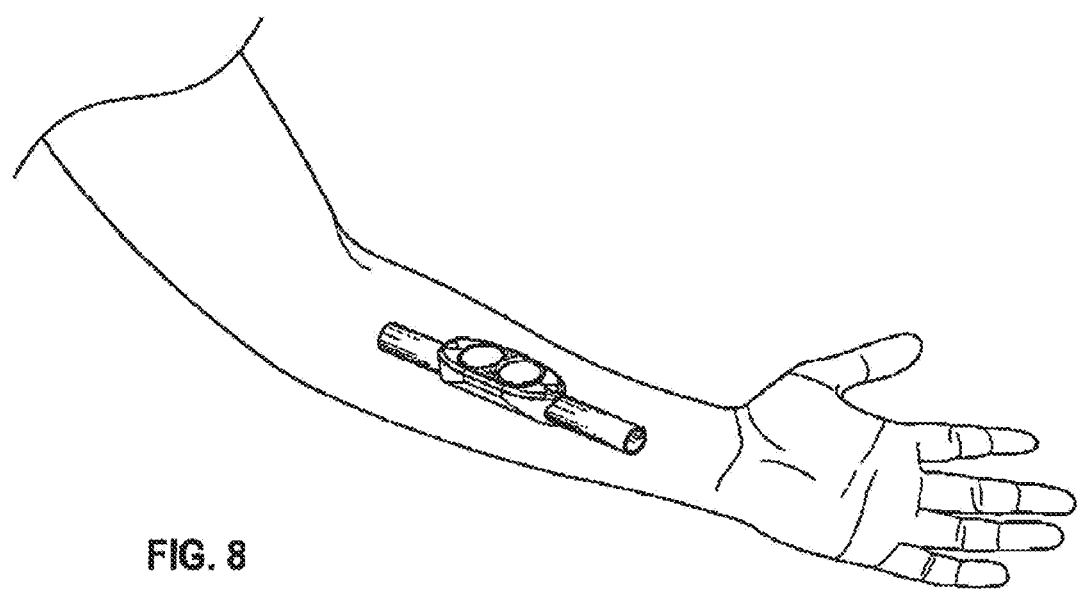
FIG. 8: A ported vascular access channel with graft implanted in patient's arm in an embodiment.

In FIG. 5 along cross-section 37" the upper and lower portions 44', 45' complete surround vessel 4 along a 360 degree perimeter. In other embodiments upper and lower portions 44', 45' may still surround vessel 4 but to a lesser extent than 360 degrees.

Returning to FIG. 3, the first portion includes a port that includes a funnel 35 with a funnel surface 18 that narrows as the funnel surface approaches the central chamber. The central chamber includes a central longitudinal axis 36 (see also 36' or 36" of FIGS. 5 and 7C) and the funnel includes a central vertical axis 37 (see also 37' of FIG. 5) that is orthogonal to the longitudinal axis. The second portion includes a hardened, non-compliant surface 9 that intersects the vertical axis 37'. This helps prevent through-and-through punctures of vessel 4.

Figure 16:
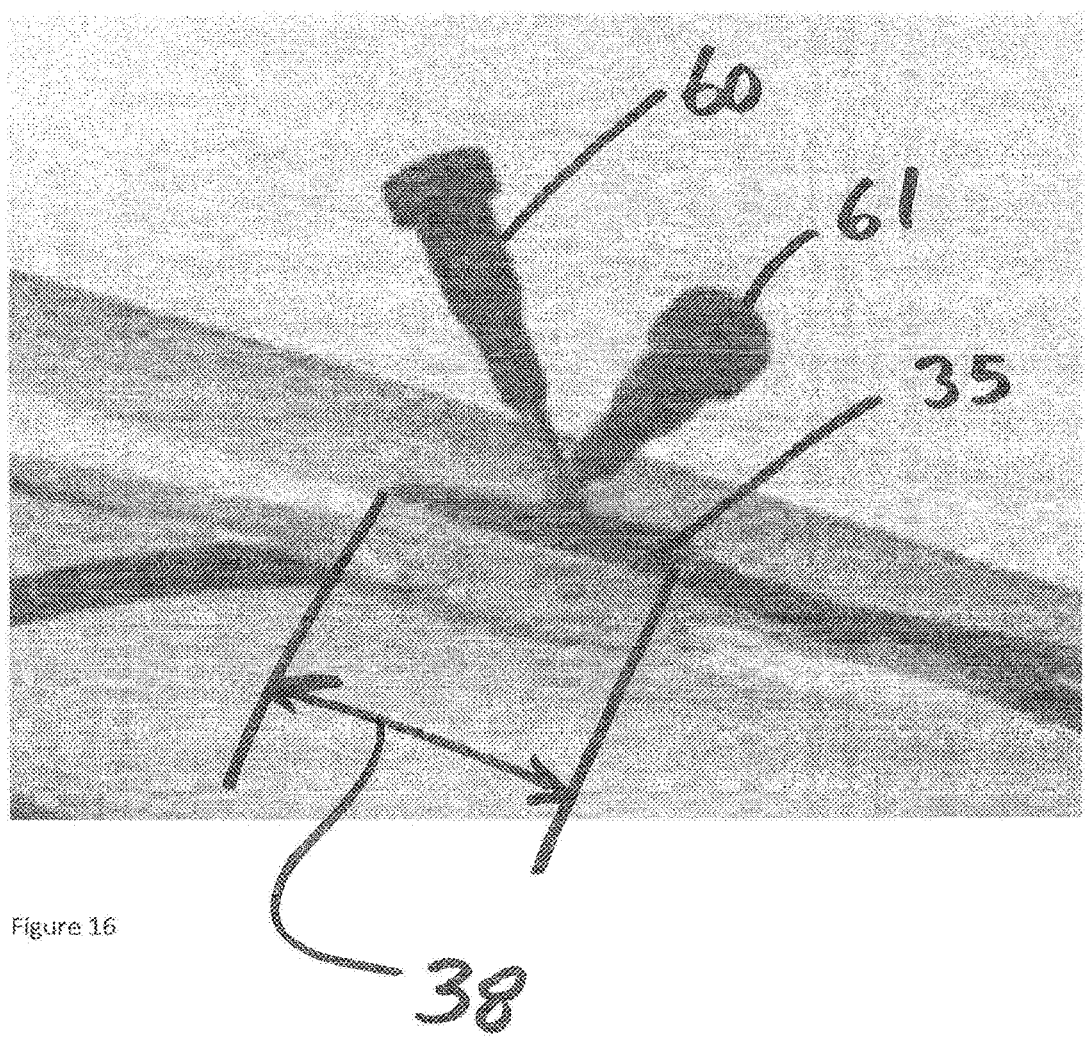
FIG. 16: A funnel accommodating two directionally opposed needles in an embodiment.

In an embodiment the funnel includes a length 38 that is parallel to the central longitudinal axis and a width 39 that is orthogonal to the central longitudinal axis; and the length is greater than the width. For example, FIG. 3 illustrates an oblong funnel whereas FIG. 4 illustrates circular funnels. The use of the oblong funnel illustrates a funnel "configured to" simultaneously accommodate both blood intake and blood return penetration members. For example, see FIG. 16. Because funnel 35 is largely orthogonal to the vessel 34 and has appropriate length 38 two opposing needles 60, 61 are accommodated. This is in contrast to systems where the funnel forms an acute angel with longitudinal axis 36 such that the needle in the funnel is largely directed either upstream or downstream to flow in a vessel. FIG. 16 shows two needles collectively positioned upstream and downstream to a vessel.

In an embodiment the funnel includes a tissue scaffold that substantially fills the funnel. For example, see element 8 of FIG. 4. However, in other embodiments the matrix or scaffold may not fill the funnel but merely occupy some space within the funnel. This would be the case when scaffold of 88 (FIG. 14) is inserted into chamber 124 (FIG. 13) of upper portion 121' (or into chamber 124' of upper piece 121 of FIG. 12).

In an embodiment the tissue scaffold includes one or more of a foam, a polyurethane foam, a hydrogel, poly ethylene glycol (PEG), polyglycolic acid (PGA), polylactic acid (PLA), poly(lactic-co-glycolic acid) (PLGA), glutaraldehyde adhesives, fibrin sealants, cyanoacrylates, collagenous compounds, electrospun fabrics, and decellularized extracellular matrix. In an embodiment an adhesive (e.g., cyanoacrylate glue) couples the tissue scaffold to the funnel surface 18.

In an embodiment outer surfaces 40, 41 of the first and second portions 44, 45 are porous or are finished in any manner that promotes tissue ingrowth (e.g., roughened, corrugated). In an embodiment, inner surfaces of the first and second portions 44, 45 (e.g., surfaces of the first and second portions which come into contact with the vessel), in addition to or instead of outer surfaces of the first and second portions 44, 45, are porous or are finished in any manner that promotes tissue ingrowth (e.g., roughened, corrugated). Such inner surfaces may include, for example, area 6 of FIG. 4.

An embodiment comprises a tissue scaffold included within a subportion of the first portion, and the subportion is between the central chamber and a proximal opening of the funnel. For example, see portion 47 of FIG. 12. Subportion 47 may include slot 124' but in other embodiments there may be no such slot and the scaffold may provide a resistive fit between the vessel and upper portion 121.

Embodiments described herein provide the first and second portions are configured to fixedly couple to each other but not to the vessel. For example, with FIG. 12 portion 122 includes a male member 77 and portion 121 includes a female member 78 to receive the male member and couple the first and second portions to each other. In doing so, portion 121 may couple flush to surface 125 but in other embodiments may not do so. Further, while portions 121, 122 couple to one another "fixedly" (e.g., using male/female coupling) those portions may only couple to the vessel with a resistive fit. That resistive fit may be due to a cell scaffold between the vessel and portions 121, 122 or the portions 121, 122 may be sized such that the central chamber they provide may provide a resistance fit with the vessel. Further, no portion of the port needs to be sutured to the vessel. This may avoid damage to the vessel and/or allow for future size changes to the vessel. For example, the port may couple to a fistula soon after fistula formation and before full fistula maturation. Further, this may accommodate future balloon angioplasty of the vessel.

Regarding coupling the port to vessel, in an embodiment the first and second portions rotationally and slideably couple to the vessel when implanted. For example, in FIG. 3 portions 44, 45 may rotate 53 about axis 36 and/or slide parallel to axis 36 considering they may only have a resistance fit with vessel 34 instead of being sutured thereto.

In an embodiment, portions may be sutured together. For example, in FIG. 12 suture in channels 49, 50 may couple pieces 121, 122 together. The suture may be in addition to or instead of members 77, 78. The sutures may be biodegradable such to accommodate future vessel expansion. In other words, in an embodiment the first and second portions include outer surfaces having channels 49, 50 that align with one another when the first and second portions couple to each other.

In an embodiment the coupling mechanism between portions may also fixedly couple a cellular scaffold to the portions. For example, with FIG. 12 male member 77 intersects a subportion 124' of the first portion 121 when coupled to the female member 78. When scaffold 88 (FIG. 14) is in slot 124' the male member would hold scaffold 88 in place.

In an embodiment an additional tissue scaffold may be included within an additional subportion of the second portion (e.g., portion 48 of portion 122 of FIG. 12), and the additional subportion is between the central chamber and wall of the second portion.

In an embodiment, the central chamber 46 forms a conduit that receives the vessel (see FIG. 5).

In an embodiment the first portion includes an additional port 2' (FIG. 2) that includes an additional funnel with an additional funnel surface that narrows as the additional funnel surface approaches the central chamber; the additional funnel includes an additional central vertical axis that is orthogonal to the longitudinal axis; and the hardened, non-compliant surface that intersects the additional vertical axis.

In an embodiment, the funnel surface 18 includes: (a) a distal wall surface 51 that slopes proximally as the distal surface approaches the central chamber, and (b) a proximal wall surface 52 that slopes distally as the proximal surface approaches the central chamber (FIG. 3).

In an embodiment, the funnel surface 18 is treated to promote tissue ingrowth. In an embodiment the funnel surface includes an attachment surface selected form the group comprising: a porous surface, a dimpled surface, and a tissue scaffold adhered to the attachment surface.

In an embodiment (FIG. 5), the first portion 44' includes first and second ports 3, 3' separate from the port 8, and the first port includes a first central axis 55 forming an acute angle 56 with the central longitudinal axis 36' of the central chamber and the second port includes a second central axis 54 forming an obtuse angle 57 with the central longitudinal access of the central chamber.

More examples now follow.

Example 1 includes a vascular port comprising: first and second portions that are not monolithic with each other; wherein: (a)(i) the first portion includes a first arcuate surface to contour to a first portion of a vessel and the second portion includes a second arcuate surface to contour to a second portion of the vessel; (a)(ii) the first and second portions couple to one another around the vessel when implanted to form a central chamber that houses the vessel; (a)(iii) the first portion includes a port that includes a funnel with a funnel surface that narrows as the funnel surface approaches the central chamber; (a)(iv) the central chamber includes a central longitudinal axis and the funnel includes a central vertical axis that is orthogonal to the longitudinal axis; (a)(v) the second portion includes a hardened, non-compliant surface that intersects the vertical axis.

The first and second portions may be top and bottom portions or may both be side portions in various embodiments.

Example 2 includes the port of 1 wherein: the funnel includes a length that is parallel to the central longitudinal axis and a width that is orthogonal to the central longitudinal axis; and the length is greater than the width.

Example 3 includes the port of example 1 wherein the funnel includes a tissue scaffold that substantially fills the funnel.

Example 4 includes the port of example 1, wherein the tissue scaffold includes a member selected from the group comprising: a foam, a polyurethane foam, a hydrogel, poly ethylene glycol (PEG), polyglycolic acid (PGA), polylactic acid (PLA), poly(lactic-co-glycolic acid) (PLGA), glutaraldehyde adhesives, fibrin sealants, cyanoacrylates, collagenous compounds, electrospun fabrics, and decellularized extracellular matrix.

Example 5 includes the port of example 1 comprising an adhesive that couples the tissue scaffold to the funnel surface.

Example 6 includes the port of example 1, wherein outer surfaces of the first and second portions are porous.

Another version of Example 6 includes the port of example 1, wherein any surfaces of the first and second portions are porous.

For instance, in addition to or instead of outer surfaces of the first and second portions, the inner surfaces of the device may also have porous portions (e.g., along the central axis) in order to promote tissue attachment. Such inner surfaces may include, for example, area 6 of FIG. 4.

Example 7 includes the port of example 1 comprising a tissue scaffold included within a subportion of the first portion, and the subportion is between the central chamber and a proximal opening of the funnel.

Example 8 includes the port of example 7 wherein at least one of the first and second portions includes a male member and another of the first and second portions includes a female member to receive the male member and couple the first and second portions to each other.

Example 9 includes the port of example 8, wherein the male member intersects the subportion of the first portion when coupled to the female member.

Example 10 includes the port of example 7 comprising an additional tissue scaffold included within an additional subportion of the second portion, and the additional subportion is between the central chamber and wall of the second portion.

Example 11 includes the port of example 1 wherein the central chamber forms a conduit that receives the vessel.

Example 12 includes the port of example 1, wherein: (a)(i) the first portion includes an additional port that includes an additional funnel with an additional funnel surface that narrows as the additional funnel surface approaches the central chamber; (a)(iv) the additional funnel includes an additional central vertical axis that is orthogonal to the longitudinal axis; (a)(v) the hardened, non-compliant surface that intersects the additional vertical axis.

Example 13 includes the port of example 1, wherein the first and second portions include outer surfaces having channels that align with one another when the first and second portions couple to each other.

Example 14 includes the port of example 1, wherein the first and second portions are configured to fixedly couple to each other but not to the vessel.

Example 15 includes the port of example 1, wherein the funnel surface includes: (a) a distal wall surface that slopes proximally as the distal surface approaches the central chamber, and (b) a proximal wall surface that slopes distally as the proximal surface approaches the central chamber.

Example 16 includes the port of example 1, wherein the funnel surface is treated to promote tissue in growth.

Example 17 includes the port of example 16, wherein the funnel surface includes an attachment surface selected from the group comprising: a porous surface, a dimpled surface, and a tissue scaffold adhered to the attachment surface.

Example 18 includes the port of example 1, wherein the funnel is configured to simultaneously accommodate both blood intake and blood return penetration members.

Example 19 includes the port of example 1, wherein the first and second portions rotationally and slideably couple to the vessel when implanted.

Example 20 includes the port of example 1, wherein the first and second portions couple to one another via at least one biodegradable coupler.

Example 21 includes the port of example 20, wherein the biodegradable coupler includes suture.

Example 22 includes the port of example 1, wherein the first and second portions couple to one another around the vessel and collectively couple to the vessel via a resistance fit and the first and second portions are not configured to couple to the vessel via sutures.

Example 23 includes the port of example 1, wherein the first portion includes first and second ports separate from the port, and the first port includes a first central axis forming an acute angle with the central longitudinal access of the central chamber and the second port includes a second central axis forming an obtuse angle with the central longitudinal axis of the central chamber.

Example 24 includes an apparatus comprising: first and second portions that are monolithic with each other; and a vessel; wherein: (a)(i) the first portion includes a first arcuate surface to contour to a first portion of the vessel and the second portion includes a second arcuate surface to contour to a second portion of the vessel; (a)(ii) the first and second portions couple to one another around the vessel to form a central chamber that houses the vessel; (a)(iii) the first portion includes a port that includes a funnel with a funnel surface that narrows as the funnel surface approaches the central chamber; (a)(iv) the central chamber includes a central longitudinal axis and the funnel includes a central vertical axis that is orthogonal to the longitudinal axis; (a)(v) the second portion includes a hardened, non-compliant surface that intersects the vertical axis.

Some embodiments may ship to a medical facility with a graft or catheter already coupled to the port device and/or the port device may later be coupled to such a graft or catheter.

While a "needle" is addressed periodically herein embodiments may work with access devices in general that permit access and transportation of fluid. Such embodiments include conduits of 14 to 20 gauge for example. Also, a "vessel" as used herein may be tissue or synthetic vessel, catheter, and/or graft and the like.

An embodiment includes a kit including various ports wherein the size and/or shape (FIG. 1 vs. FIG. 9) of the central chamber of the ports may change to accommodate varying anatomical features.

While the present invention has been described with respect to a limited number of embodiments, those skilled in the art will appreciate numerous modifications and variations therefrom. It is intended that the appended claims cover all such modifications and variations as fall within the true spirit and scope of this present invention.

The invention claimed is:

1. A vascular access device comprising:
a top portion; and
a bottom portion,
wherein:
the top portion and the bottom portion are not monolithic with each other;
the top and bottom portions are configured to couple to one another around an entire 360° perimeter of a portion of a vessel when implanted to form a central chamber that houses the entire 360° perimeter of the portion of the vessel between a first surface of the top portion and a second surface of the bottom portion;
the top portion includes an opening that allows a needle to pass through;
the central chamber includes a central longitudinal axis and the opening includes a central vertical axis that is orthogonal to the central longitudinal axis; and
the second surface of the bottom portion is a hardened, non-compliant surface that extends through the central vertical axis when the top and bottom portion are coupled to one another.

2. The device of claim 1, wherein outer surfaces of the top and bottom portions are porous.

3. The device of claim 1, further comprising a first tissue scaffold included within a subportion of the top portion and an second tissue scaffold included within a subportion of the bottom portion, wherein the subportion of the top portion is between the central chamber and the opening of the top portion and the subportion of the bottom portion is between the central chamber and a wall of the bottom portion.

4. The device of claim 1, wherein at least one of the top and bottom portions includes a male member and another of the top and bottom portions includes a female member that is configured to receive the male member and couple the top and bottom portions to each other.

5. The device of claim 1, wherein the top and bottom portions include outer surfaces having channels that are configured to align with one another when the top and bottom portions couple to each other.

6. The device of claim 1, wherein the top and bottom portions are configured to rotationally and slidably couple to the portion of the vessel when implanted.

7. The device of claim 1, wherein the top and bottom portions are configured to couple to one another around the portion of the vessel and collectively couple to the portion of the vessel via a resistance fit and the top and bottom portions are not configured to couple to the portion of the vessel via sutures.

8. The device of claim 1, wherein the top portion further includes first and second passages separate from the opening, and the first passage includes a first central axis forming an acute angle with the central longitudinal axis of the central chamber and the second passage includes a second central axis forming an obtuse angle with the central longitudinal axis of the central chamber.

9. The device of claim 1, wherein outer surfaces of the top and bottom portions are roughened.

10. The device of claim 1, wherein the top portion includes a first arcuate surface and the bottom portion includes a second arcuate surface, wherein the first arcuate surface of the top portion and the second arcuate surface of the bottom portion are contoured to minimize impact on the portion of the vessel.

11. The device of claim 1, wherein the top and bottom portions are configured to couple to one another via at least one biodegradable coupler.

12. The device of claim 11, wherein the at least one biodegradable coupler includes a suture.

13. A method of using a vascular access device, wherein the vascular access device comprises:

a top portion; and a bottom portion, wherein:

the top portion and the bottom portion are not monolithic with each other;

the top and bottom portions are configured to couple to one another around an entire 360° perimeter of a portion of a vessel when implanted to form a central chamber that houses the entire 360° perimeter of the portion of the vessel between a first surface of the top portion and a second surface of the bottom portion;

the top portion includes an opening that allows a needle to pass through;

the central chamber includes a central longitudinal axis and the opening includes a central vertical axis that is orthogonal to the central longitudinal axis; and the second surface of the bottom portion is a hardened, non-compliant surface that extends through the central vertical axis when the top and bottom portion are coupled to one another;

the method comprising:

inserting, through the opening in the top portion, a first needle in the vessel;

inserting, through the opening in the top portion, a second needle in the vessel;

withdrawing blood, via the first needle, from within the vessel; and returning the blood, via the second needle, to the vessel, wherein the second needle is placed upstream of the first needle in the vessel.

14. The device of claim 1, wherein the opening of the top portion is shaped to allow a plurality of needle puncture sites to pass through to contact the vessel down a length of the opening.

* * * * *